United States Patent [19]

Bierschenk et al.

[11] Patent Number: 5,300,683
[45] Date of Patent: * Apr. 5, 1994

[54] FLUORINATION OF ACETALS, KETALS AND ORTHOESTERS

[75] Inventors: Thomas R. Bierschenk; Timothy Juhlke, both of Round Rock; Hajimu Kawa; Richard J. Lagow, both of Austin, all of Tex.

[73] Assignee: Exfluor Research Corporation, Austin, Tex.

[*] Notice: The portion of the term of this patent subsequent to Apr. 13, 2010 has been disclaimed.

[21] Appl. No.: 966,681

[22] Filed: Oct. 26, 1992

Related U.S. Application Data

[63] Continuation of Ser. No. 752,703, Aug. 30, 1991, Pat. No. 5,202,480, which is a continuation of Ser. No. 413,785, Sep. 28, 1989, Pat. No. 5,053,536, which is a continuation-in-part of Ser. No. 250,384, Sep. 28, 1988, abandoned.

[51] Int. Cl.$^5$ ............................................. C07C 59/245
[52] U.S. Cl. .................................... 562/582; 562/586; 562/849; 562/850; 568/603; 568/604
[58] Field of Search ............... 562/582, 586, 849, 850; 568/603, 604

[56] References Cited

U.S. PATENT DOCUMENTS

| | | | |
|---|---|---|---|
| 3,721,696 | 3/1973 | Sianesi et al. | 260/463 |
| 3,847,978 | 11/1974 | Sianesi et al. | 260/535 |
| 4,003,941 | 1/1977 | Crawford et al. | 260/463 |
| 4,113,435 | 9/1978 | Lagow et al. | 422/191 |
| 4,275,225 | 6/1981 | Krespan | 560/174 |
| 4,647,413 | 3/1987 | Savu | 260/544 |
| 4,755,330 | 7/1988 | Viola et al. | 260/544 |
| 4,755,567 | 7/1988 | Bierschenk et al. | 525/409 |
| 4,760,198 | 7/1988 | Bierschenk et al. | 568/615 |
| 4,827,042 | 5/1989 | Lagow et al. | 568/603 |
| 4,847,427 | 7/1989 | Nappa | 568/615 |
| 4,859,747 | 8/1989 | Bierschenk et al. | 525/409 |
| 5,053,536 | 10/1991 | Bierschenk et al. | 562/582 |

FOREIGN PATENT DOCUMENTS

| | | |
|---|---|---|
| 640836 | 1/1962 | Canada . |
| 0077114 | 7/1983 | European Pat. Off. . |
| 04264 | 2/1990 | PCT Int'l Appl. . |
| 1192238 | 3/1970 | United Kingdom . |

OTHER PUBLICATIONS

Tacchi Venturi et al., "Spectroscopic Studies on the Carboxylic Acids of Some Carbonyl Fluoride Telemers," *J. Mole. Struct.*, vol. 14, pp. 293–302 (1972).
International Search Report PCT/US89/04248.

*Primary Examiner*—José G. Dees
*Assistant Examiner*—Porfirio Nazario
*Attorney, Agent, or Firm*—Hamilton, Brook, Smith & Reynolds

[57] ABSTRACT

This invention pertains to perfluoropolyethers and perhalogenated chlorofluoroether polymers that can be prepared by fluorinating polymers made by the polymerization of acetals, ketals, polyacetals, polyketals and orthoesters with elemental fluorine.

3 Claims, No Drawings

FLUORINATION OF ACETALS, KETALS AND ORTHOESTERS

RELATED APPLICATIONS

This application is a continuation of U.S. patent application Ser. No. 07/752,703, now issued as U.S. Pat. No. 5,202,480, filed Aug. 30, 1991, which is a continuation of U.S. Pat. No. 5,053,536, issued Oct. 1, 1991, which is a continuation-in-part of U.S. patent application Ser. No. 07/250,384, filed Sep. 28, 1988, now abandoned, the teachings of which are incorporated by reference herein.

BACKGROUND

Perfluoropolyethers are highly regarded in the specialty lubricant field because of their wide liquid ranges, low vapor pressures and high thermal and oxidative stabilities. Because of these properties (many of which are unique to fluorocarbons), they are excellent high performance lubricants, superior base stocks for greases, excellent lubricating oils, and heat transfer fluids. In addition, because of these uniquely outstanding properties, saturated perfluoropolyethers are of current interest as specialty sealants, elastomers and plastics.

In spite of their unlimited potential, only three perfluoropolyethers are commercially available to date because of the lack of fluorocarbon intermediates which are suitable for preparing the polymers. They are:

1. DuPont's Krytox ™ fluid which is made by polymerizing hexafluoropropylene oxide.
2. Demnum ™ fluid, a product of Daikin Industries, is obtained by ring opening polymerization of 2,2,3,3-tetrafluorooxetane using a catalyst with subsequent treatment of the highly fluorinated polyether with fluorine gas to give a perfluorinated product.
3. Montedison's Fomblin Z ™ and Fomblin Y ™ fluids which are prepared by photooxidizing tetrafluoroethylene and hexafluoropropylene oxide, respectively, in the presence of oxygen.

A process has been described for preparing perfluoropolyethers by reaction of a hydrocarbon polyether with elemental fluorine in the presence of a hydrogen fluoride scavenger. See U.S. Pat. No. 4,755,567.

SUMMARY OF THE INVENTION

This invention relates to perfluoropolyether and perhalogenated chlorofluoroether polymers that can be prepared by fluorinating polymers made by the polymerization of acetals, ketals, polyacetals, polyketals and orthoesters with elemental fluorine. The products formed by the present invention have essentially the following formula:

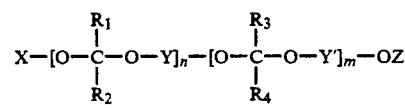

wherein Y and Y' are the same or different and are selected from the group consisting of linear and branched perfluoroalkylenes having at least 2 carbon atoms; perfluoroalkyleneoxyalkylene and perfluoropoly(alkyleneoxyalkylene) each having alkylene groups containing at least two carbon atoms wherein in Y or Y' one or more of the fluorine atoms may be substituted by a halogen atom other than fluorine; wherein X and Z are the same or different and are selected from the group consisting of $-(CF_2)_rCOF$, $-(CF_2)_rOCF_3$, $-(CF_2)_rCOOH$ and $C_rF_{2r+1-q}Cl_q$, wherein r is an integer from 1 to 12 and q is an integer from 0 to 25; wherein $R_1$, $R_2$, $R_3$ and $R_4$ are the same or different and are selected from the group consisting of $-F$, $-Cl$, $-CF_2Cl$, $-CFCl_2$, $-CCl_3$, perfluoroalkyl of one to ten carbon atoms and perfluoroalkoxyalkyl of one to ten carbon atoms wherein one or more of the fluorine atoms may be substituted by a halogen atom other than fluorine; wherein n is an integer from 2 to 1,000; and wherein m is an integer from 0 to 1,000; provided that when $R_1$, $R_2$, $R_3$ and $R_4$ together are F then Y or Y' comprises an ethylene group having at least one fluorine atom which is substituted by a halogen other than fluorine.

This invention also relates to perhalogenated polyethers of the formula:

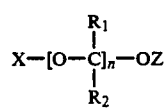

wherein $R_1$, $R_2$, X and Z are defined above and n is an integer from 2 to 1000; provided that $R_1$ and $R_2$ cannot both be fluorine atoms.

The perfluoropolyethers and the perhalogenated chlorofluoropolyethers of this invention can be used as lubricants, hydraulic fluids, thermal shock fluids, vapor phase soldering fluids and in numerous other applications in which an inert, nonflammable, oxidatively stable fluid is required. The low molecular weight perfluoropolyethers of the present invention have many useful applications in the electronics industry.

DETAILED DESCRIPTION OF THE INVENTION

In general, the perfluoropolyether and perhalogenated chlorofluoropolyether polymers have the formula:

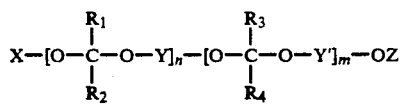

wherein Y and Y' are the same or different and are selected from the group consisting of linear and branched perfluoroalkylenes having at least 2 carbon atoms, preferably having 2 to 6 carbon atoms; perfluoroalkyleneoxyalkylene and perfluoropoly-(alkyleneoxyalkylene) each having alkylene groups containing at least two carbon atoms, preferably having from 2 to 30 carbons and most preferably having 4 to 8 carbons; wherein in Y or Y' one or more of the fluorine atoms may be substituted by a halogen atom other than fluorine. Y and Y' can be isotactic perfluoropolyethers or atactic perfluoropolyethers, such as $-CF_2CF_2CF_2$, $-CF_2CF_2CF_2CF_2-$, $-CF_2CF_2OCF_2CF_2-$, $-CF_2(CF_3)CFOCF(CF_3)CF_2-$ and $-CF_2CF_2OCF_2CF_2OCF_2CF_2-$. X and Z are the same or different and are selected from the group consisting of $-(CF_2)_rCOF$, $-(CF_2)_rOCF_3$, $-(CF_2)_rCOOH$ and $C_rF_{2r+1-q}Cl_q$, wherein r is an integer from 1 to 12 and q is an integer from 0 to 25. $R_1$, $R_2$, $R_3$ and $R_4$ are the same or different and are selected from the group consisting of —F, —Cl, —CF$_2$Cl, —CFCl$_2$, —CCl$_3$, perfluoroalkyl of one to ten carbon atoms, such as —CF$_3$, —C$_2$F$_5$, —C$_3$F$_7$ and —C$_4$F$_9$ and perfluoroalkoxyalkyl of one to ten carbon atoms, such as —OCF$_3$ and —OCF$_5$, wherein one or more of the fluorine atoms in said perfluoroalkyl and perfluoroalkoxyalkyl may be substituted by a halogen atom other than fluorine. Preferably R$_1$ to R$_4$ are F and —CF$_3$ groups. n is an integer from 2 to 1,000; and m is an integer from 0 to 1,000; provided that when R$_1$, R$_2$, R$_3$ and R$_4$ together are F then Y or Y' comprises an ethylene group having at least one fluorine atom which is substituted with a halogen atom other than fluorine, preferably by chlorine.

The n and m subscripts of formula I are average indices of composition such that when m is zero the polyether is referred to as an alternating copolymer of

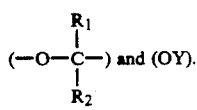

When m and n are greater than zero, the polyether is a terpolymer containing

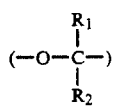

groups having random OY and OY' units along the polymer chain. The simplest member of this class of compounds is a 1:1 copolymer of difluoromethylene oxide and tetrafluoroethylene oxide which is the subject of U.S. Pat. No. 4,760,198.

This invention also relates to perfluoropolyethers and perhalogenated chlorofluoropolyethers of Formula I where Y and Y' are polyethers and have the average formula:

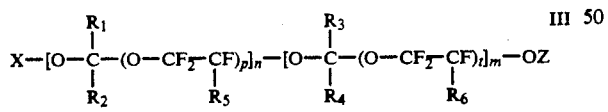

wherein R$_1$, R$_2$, R$_3$, R$_4$, R$_5$ and R$_6$ are the same or different and are selected from the group consisting of —F, —Cl, —CF$_2$Cl, —CFCl$_2$, —CCl$_3$, perfluoroalkyl of one to ten carbon atoms and perfluoroalkoxyalkyl of one to ten carbon atoms wherein one or more of the fluorine atoms may be substituted by a halogen atom other than fluorine; wherein X and Z are the same or different and are selected from the group consisting of —(CF$_2$)$_r$COF, —(CF$_2$)$_r$OCF$_3$, —(CF$_2$)$_r$COOH and C$_r$F$_{2r+1-q}$Cl$_q$ wherein r is an integer from 1 to twelve and q is an integer from 0 to 25; wherein n is an integer from 2 to 1000, m is an integer from 0 to 1000; and p and t are the same or different and are integers from 1 to 50, provided that when p and t are one and R$_1$, R$_2$, R$_3$ and R$_4$ to-gether are fluorine, then R$_5$ or R$_6$ is a group other than fluorine. Preferably, p and t are integers from 1 to 10.

Examples of perfluoropolyethers where m in formula I is zero and p is an integer between 2 and 50 are shown below:

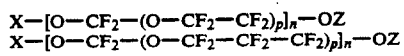
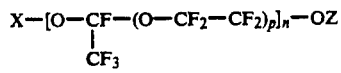
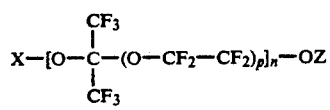

Examples of perfluorinated polyethers of formula I where m is zero, p is defined above and Y is an isotactic perfluoropolyether or atactic perfluoropolyether are:

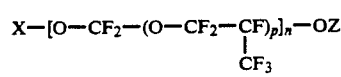
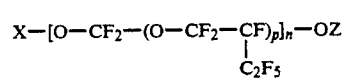
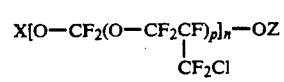

Examples of random copolymers of formula I in which m and n are greater than zero, and p is defined above, include:

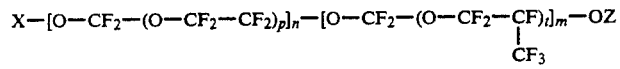
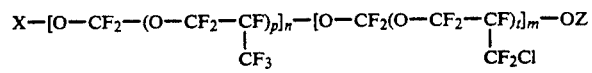

Perfluoropolyethers and perhalogenated chlorofluoropolyethers can also be prepared which have the average formula:

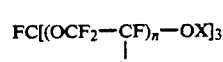    IV or

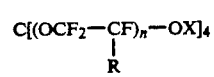    V wherein X is selected from the group consisting of —(CF$_2$)$_r$COOH, —(CF$_2$)$_r$OCF$_3$, —(CF$_2$)$_r$COF, and C$_r$F$_{2r+1-q}$Cl$_q$ where r is an integer from 1 to 12 and q is an integer from 0 to 25. Preferably X is —CF$_3$, —C$_2$F$_5$, —CF$_2$COOH, —CF$_2$OCF$_3$ and CF$_2$COF; wherein n is an integer from 1 to 50; and wherein R is selected from the group consisting of —F, —CF$_2$Cl, —CFCl$_2$, CCl$_3$ and perfluoroalkyl of one to ten carbons.

This invention further pertains to perfluoropolyethers and perhalogenated chlorofluoropolyethers having the average formula:

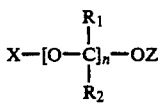

wherein $R_1$, $R_2$, X and Z are defined above, and n is an integer from 2 to 1000; provided that $R_1$ and $R_2$ cannot both be fluorine atoms.

This invention further pertains to a method of making perhalogenated formal, acetal, ketal and orthocarbonate compounds and perfluoropolyether and perhalogenated chlorofluoropolyether polymers thereof. The compounds are made by fluorination of acetal, ketal, formal or orthocarbonate hydrocarbon percursors.

The reaction of a diol with either an aldehyde, acetal, ketal or trialkyl orthoesters can be used to give a polyether if the starting materials and reaction conditions are carefully chosen. For example, if an aldehyde such as formaldehyde, acetaldehyde or butyraldehyde is reacted with a diol, a linear polyether can be made. Such a reaction is shown in Equation (1) below:

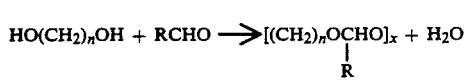

(1)

Suitable diols include ethylene glycol, diethylene glycol, triethylene glycol, tetraethylene glycol, other higher polyethylene glycols, propylene glycol, dipropylene glycol, tripropylene glycol, 2,2-dimethyl 1,3-propanediol, 1,4-butanediol, 1,5-pentanediol, 1,6-hexanediol, 1,7-heptanediol, 1,8-octanediol, 1,9-nonanediol, and 1,10-decanediol. Suitable aldehydes include formaldehyde, paraformaldehyde, 1,3,5-trioxane, acetaldehyde and its trimer, butyraldehyde and its trimer, pentanal, hexanal, 2-ethyl butanal, chloroacetaldehyde, dichloroacetaldehyde and trichloroacetaldehyde.

An alternative means of preparing the same polymer involves the reaction of an acetal with a diol. The synthesis involves the initial preparation of an acetal by reaction of an alcohol with the aldehyde as shown in Equation (2) below:

$$RCHO + 2R'OH \rightarrow (R'O)_2C(R)H + H_2O \quad (2)$$

The acetal interchange is followed by a smoothly reversible reaction in acid media giving rise to the polyacetal. This reaction is given in Equation (3) below:

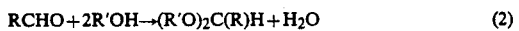

(3)

Suitable acetals include the diethyl, dipropyl, dibutyl, dipentyl and diphenyl acetals of all of the previously mentioned aldehydes.

A well known reaction which is particularly well suited for preparing copolymers of acetaldehyde involves the reaction of divinyl ethers with diols. For example, ethylene glycol divinyl ether will react with ethylene glycol in the presence of H+ at $-10°$ C. to give a 1:1 copolymer of ethylene glycol and acetaldehyde. Similarly, the divinyl ether of 1,5-pentanediol will react with 1,5-pentanediol to give a copolymer of pentanediol and acetaldehyde:

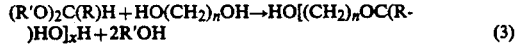

(4)

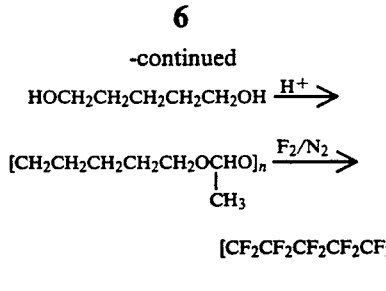

Terpolymers can be prepared by reacting a divinyl ether of one diol with a diol of a different structure. For example, the divinyl ether of ethylene glycol will react with 1,3-propanediol to yield a polyether after fluorination having the following structure:

The divinyl ethers are conveniently formed by reacting a dihydroxyl terminated compound with acetylene at 160° C. in the presence of KOH as shown below in Equation (5).

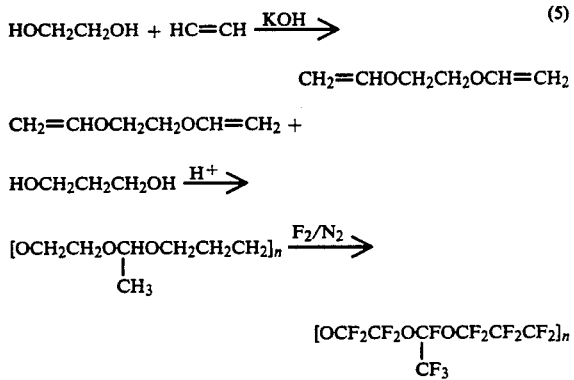

A variety of aldehydes can be polymerized and fluorinated to give perfluoropolyethers that have unique and often useful properties. For example, chloroacetaldehyde can be polymerized and fluorinated to give perfluoropolychloroacetaldehyde. Similarly, dichloroacetaldehyde and trichloroacetaldehyde can be polymerized and fluorinated to give the perfluorocarbon analog of the polyethers. Chlorofluoroethers such as these are potentially useful nonflammable aircraft hydraulic fluids. Their relatively high oxidative stability and low compressibility make them attractive candidates. Other aldehydes such as acetaldehyde, trifluoroacetaldehyde and propanal can be polymerized and fluorinated to give stable polymers.

Ketals undergo a facile reversible metathesis reaction with alcohols to give polyketals as shown below in Equation (4):

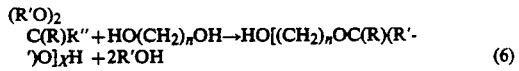

(6)

The list of useful ketals would include 2,2-dimethoxypropane, 2,2-dimethoxybutane, 2,2-dimethoxypentane, 2,2-dimethoxyhexane, 3,3-dimethoxypentane, 3,3-dimethoxyhexane as well as the diethoxy, dipropoxy, dibutoxy and diphenoxy analogues of the previously mentioned ketals.

The direct reaction of a ketone with an alcohol, a reaction analogous to the reaction of an aldehyde with an alcohol, generally works only for several isolated ketones. For this reason, the ketal is normally used.

The reaction of a trialkyl or triaryl orthoester with alcohols gives formates according to the reaction presented in Formula (5):

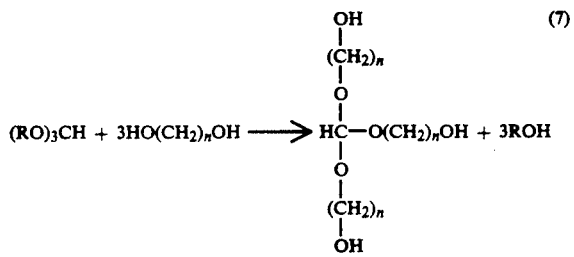

Useful orthoesters include trimethylorthoformate, triethylorthoformate, tripropylorthoformate, tributylorthoformate, triphenylorthoformate, trimethylorthoacetate, triethylorthoacetate, tripropylorthoacetate, tributylorthoacetate, triphenylorthoacetate, trimethylorthopropionate, triethylorthopropionate, tripropylorthopropionate, tributylorthopropionate, triphenylorthopropionate, trimethylorthobutyrate, triethylorthobutyrate, tripropylorthobutyrate, tributylorthobutyrate and triphenylorthobutyrate.

It should be clear from the preceeding discussions that a wide variety of linear as well as highly branched polyethers can be made using these interchange reactions. By carefully choosing the appropriate diol and aldehyde it is possible to prepare cyclic acetals which can often be polymerized to give polyethers. For example, formaldehyde reacts with diethylene glycol to give 1,3,6-trioxocane which can be polymerized to give linear polyacetals as shown in Formula (6) below:

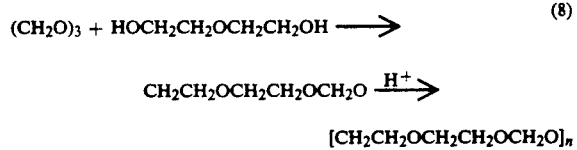

Similarly, the cyclic products formed by the reaction of trimethylene glycol with dibutyl formal and the reaction of hexamethylene glycol with propionaldehyde polymerize in the presence of an acid to given linear polymers as described in U.S. Pat. No. 2,071,252. In general, if the glycol is 1,4-butanediol or higher a linear polymer is formed whereas glycols having fewer carbons generally form rings. If the glycol used is a polyether glycol, such as diethylene glycol or triethylene glycol, the linear polymer represents a thermodynamically more stable structure. However, it is often possible to convert the linear polyether to the cyclic ether by vacuum pyrolysis.

Conversion of the hydrocarbon polyether to a perfluoropolyether can be accomplished by reacting the polyether with elemental fluorine. Because of the reactive nature of elemental fluorine, it is preferably to dilute the fluorine with an inert gas such as nitrogen or helium. Typically, the fluorine is diluted with nitrogen and as higher degrees of fluorination are achieved, the concentration of fluorine is usually increased. Due to the extreme exothermicity of the reaction, the fluorination must be carried out slowly unless provisions have been made for rapidly removing the heat of reaction. Submersion of the reactor in a cooled liquid bath is usually adequate for achieving commercially acceptable rates of reaction.

Fluorine gas is the preferred fluorinating agent and is commercially available at sufficiently high purity levels and at an acceptable cost. The fluorination reaction is generally carried out at a temperature between $-40°$ and $+150°$ C., preferably between $-10°$ and $+50°$ C. It can be carried out in a reactor containing an ultraviolet radiation source or in the dark. Using the preferred temperature range, it is not necessary to have an ultraviolet light source since the fluorine is sufficiently reactive. If an ultraviolet light source is used, however, a wavelength between 250 and 350 nm is preferred. When the reactor is irradiated with an external light source, a transparent window is needed which does not react with either fluorine or hydrogen fluoride. A quartz lens coated with a thin film of fluorinated ethylene-propylene copolymer works well.

The fluorination reaction can be carried out in a variety of ways. The polyether can be coated on sodium fluoride powder to give a free-flowing powder which can be fluorinated in either a stationary tube, in a rotating drum-type reactor, or in a fluidized bed. See U.S. Pat. No. 4,755,567 and U.S. Pat. No. 4,859,747, the teachings of which are incorporated herein by reference.

Alternatively, the polyether, if soluble, can be dissolved in a solvent inert to fluorine and can be fluorinated while in solution using a liquid phase fluorination reactor. See U.S. patent application Ser. No. 07/250,376, entitled "Liquid Phase Fluorination", by Thomas R. Bierschenk, Timothy Juhlke, Hajimu Kawa and Richard J. Lagow, filed Sep. 28, 1988, and U.S. Pat. No. 5,093,432, which is a continuation-in-part of U.S. Ser. No. 07/250,376, the teachings of each are incorporated by reference herein. A typical laboratory-size reactor for example, has a volume of about 10 liters and contains approximately 2 to 8 liters of a suitable solvent. Perhalogenated chlorofluorocarbons are typically used as the fluorine-inert fluorination medium. However, perfluorocarbons, such as Fluorinert ™ FC75 [3M Corporation; mixture of perfluoro(2-butyltetrahydrofuran) and perfluoro(2-n-propyltetrahydropyran)] and perhalogenated chlorofluoropolyethers may also be used as the liquid phase fluorination medium. One preferred fluorination medium is 1,1,2-trichlorotrifluoroethane since it does not react appreciably with fluorine when the preferred temperature range is used (above the melting point of the material and below the temperature at which the fluorine reacts with it). Other fluorinated solvents can be used, such as perfluoroamines, perfluoroalkanes, low molecular weight polyethers, etc.

During a typical reaction, the polyether is fed into the reactor at a rate of 10 to 60 grams per hour. Fluorine gas is delivered to the vigorously stirred reactor at a rate sufficient to react with all of the organic feed plus an additional 5 to 10 percent. Typically the fluorine gas is diluted with an inert gas such as nitrogen. This is of particular importance if a liquid fluorination medium such as 1,1,2-trichlorotrifluoroethane is used. It is imperative to keep the fluorine concentration low so that the liquid fluorination medium and fluorine in the vapor space do not form a flammable mixture. The flammability limits of various solvents in fluorine gas can be determined by spark testing. In a typical reaction, a fluorine concentration of 10 to 40% works well. If operating properly, the fluorine concentration in the exit gas will be between 2 and 4%.

Fluorination can be carried out either in a batch mode where all of the polyether is dissolved in a solvent prior to fluorination or in a continuous mode where the polyether is continuously being pumped into the solvent as fluorine is being bubbled through the solution. Generally speaking, the continuous operation gives a preferred yield, better product quality and improved rates.

If the polyether is insoluble in the liquid fluorination medium it can still be fluorinated in high yield as an emulsion in the liquid phase reactor. An emulsified solution of the polyether and the fluorine-inert liquid fluorination medium can either be pumped into the reactor or the reactant can be emulsified in the reactor with the fluorination medium prior to the reaction.

An alternative method for fluorinating polyethers which are insoluble in the liquid fluorination medium involves adding a solvent to the polyether which allows limited solubility of polyether in the liquid fluorination medium. For clarity, 1,1,2-trichlorotrifluoroethane has been selected as the liquid fluorination medium; however, other highly fluorinated solvents can also be used. Typically, a mixture containing one part polyether, one part solvent and one part 1,1,2 trichlorotrifluoroethane will give a homogeneous solution. A solvent is selected which readily dissolves the polyether. Often it is possible to choose a solvent which will consume little, if any, of the fluorine gas. Trifluoroacetic anhydride, trifluoroacetic acid, chloroform, 1,1,2-trichloroethylene and 1,1,2-trichloroethane work especially well and have high solvating power.

The polyether/solvent/1,1,2-trichlorotrifluoroethane solution is metered into a vigorously stirred fluorination reactor. As the polyether solution contacts the 1,1,2-trichlorotrifluoroethane in the reactor, an emulsion is formed. The polyether droplets in the solution are in most cases sufficiently small and react quickly with the fluorine gas with negligible side reactions.

When carrying out the reaction in a liquid fluorination medium, a hydrogen fluoride scavenger such as sodium fluoride or potassium fluoride may or may not be present in the solution to scavenge the by-product hydrogen fluoride. However, the preferred mode of carrying out the fluorination reaction is with a sufficient quantity of sodium fluoride being present to complex with all of the hydrogen fluoride formed. When fluorinating ethers in the presence of sodium fluoride, improved yields are obtained while chain cleavage and rearrangements are minimized. See U.S. Pat. No. 4,755,567, the teachings of which are incorporated herein by reference.

Products produced using the methods just described usually have a residual hydrogen content of 0.001% or less. In order to obtain a fluid which is essentially free of residual hydrogen and void of any reactive terminal groups such as acyl fluoride groups resulting from chain degradation reactions, a final fluorination near 175° C. with 30% fluorine for several hours works well.

The following examples will further illustrate the invention, but are not to be construed as limiting its scope.

Example 1

A mixture of 1060 g diethylene glycol (10 mol), 210 g paraformaldehyde (7 mol), 500 ml benzene and 10 g acidic ion exchange resin was refluxed for 6 hours in a 2 liter flask equipped with a water separator and a reflux condenser. The solution was filtered to remove the acid catalyst and the benzene was removed by distillation. Upon removal of all of the benzene, several drops of sulfuric acid were added to the polymer and the temperature was raised to approximately 140° C. The entire contents of the flask were distilled at 160° C. with a reduced pressure (25 mm). Redistillation of the high boiling fraction gave 463 grams of 1,3,6-trioxocane (78% conversion).

Polymerization of 450 g of 1,3,6-trioxocane was carried out at room temperature in 1 liter dry methylene chloride using 0.04 ml of trifluoromethane sulfonic acid as a catalyst. The polymerization was complete in 24 hours at which time 1 g of sodium methoxide dissolved in 50 ml of dry methanol was added to neutralize the acid catalyst. 3600 g sodium fluoride powder was added to the polymer along with an additional 1 liter of methylene chloride. The mixture was stirred, the methylene chloride was allowed to evaporate and the remaining solids were ground to a powder. The polymer-coated sodium fluoride was placed in a 20 liter rotating drum reactor and dried under a stream of inert gas (e.g., nitrogen) for a period of 12 hours. The mixture was then exposed to 500 cc fluorine diluted with 2 liters of nitrogen for approximately 30 hours at 25° C. Next, the nitrogen flow was reduced to 1 liter/min and the reaction was allowed to continue for an additional 12 hours after which time the reactor was slowly warmed to 70° C. over a 6 hour period. Treatment with pure fluorine for several hours at 70° C. gave a product which contained very few hydrogen atoms. Extraction of the reaction product with 5 liters of 1,1,2-trichlorotrifluoroethane gave 386 grams of fluid (34%). Washing of the solids with 100 liters of water resulted in the isolation of 430 grams of an elastomeric solid (38% yield). The crude fluid was treated with 30% fluorine at 260° C. for 12 hours to remove the last remaining hydrogens. The fluid was distilled to give the following fractions:

| b.p. range (°C.) | Weight fraction (g) | % of total | Kinematic Viscosity (cst.) 20° C. | 80° C. |
|---|---|---|---|---|
| <200° C. at 100 mm | 120 | 31 | 3.2 | 1.07 |
| >200° C. at 100 mm <245° C. at 10 mm | 126 | 33 | 11.8 | 2.83 |
| >245° C. at 10 mm <288° C. at 0.05 mm | 62 | 16 | 38.9 | 7.06 |
| >288° C. at 0.05 mm <370° C. at 0.05 mm | 39 | 10 | 83.3 | 13.1 |
| >370° C. at 0.05 mm | 39 | 10 | 290.3 | 39.5 |

The $^{19}$F data and elemental analysis were consistent with the structure:

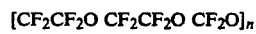

[CF$_2$CF$_2$O CF$_2$CF$_2$O CF$_2$O]$_n$

Example 2

In this example the fluid prepared in Example 1 was prepared using an alternate method which was better suited for preparing fluids while the method described in Example 1 yields a considerable amount of polymeric solids.

Into a 1 liter stirred flask equipped with a water separator were placed 500 g diethylene glycol (4.7 mol), 90 g diethylene glycol methyl ether (10.75 mol), 225 g paraformaldehyde (7.5 mol), 150 ml toluene and 5 g ion exchange resin (H+ form). The mixture was refluxed for several hours to remove the water formed during the reaction. The solution was first filtered to remove the ion exchange resin, then distilled to 150° C. at 0.05 mm/Hg to remove the toluene and other lights. A nearly quantitative yield of polymer having an average molecular weight of 1500 was obtained.

320 g of polymer, mixed with 170 g chloroform and 300 g 1,1,2-trichlorotrifluoroethane were slowly pumped over a 23 hour period into a 15 liter stirred fluorination reactor containing 6 liters of 1,1,2-trichlorotrifluoroethane and 1300 g of sodium fluoride powder. 20% fluorine was bubbled through the liquid fluorination medium at a rate 15% higher than that required to theoretically replace all of the hydrogen on the hydrocarbon being pumped into the reactor. The reactor temperature was maintained between 0° and +10° C. throughout the reaction. Following the reaction, the reactor contents were filtered and the liquid fluorination medium (1, 1, 2-trichlorotrifluoroethane) was removed from the filtrate via an atmospheric distillation to 120° C. to give 535 g of crude fluid (66%). Fluorination of the fluid at 260° C. gave a clear, colorless fluid which was shown by elemental analysis and $^{19}F$ NMR to have the following structure:

$$[CF_2CF_2OCF_2CF_2OCF_2O]_n$$

Example 3

100 g triethylene glycol (0.67 mol), 28.5 g paraformaldehyde (0.95 mol), 100 ml benzene and 1 g ion exchange resin (H+ form) were placed in a 500 ml stirred flask equipped with a water separator and a reflux condenser. The solution@was-allowed to reflux for 6 hours while the water was continuously removed. Upon removal of the water, the solution was filtered to remove the acid catalyst. Atmospheric distillation of the filtrate followed by a reduced pressure distillation (100 mm Hg) to 120° C. was used to remove the benzene solvent as well as any lights present.

Twenty grams of the viscous polymer were mixed with approximately 100 ml of methylene chloride and 120 g sodium fluoride powder (200 mesh). The resulting paste was dried in a vacuum oven at 60° C. for several hours prior to grinding to a coarse powder (approximately 30 mesh). The powder was placed in a 1 liter rotating brass reactor and was purged with 200 cc of dry nitrogen for several hours prior to the fluorination. The reactor was cooled to 0° C., the nitrogen flow was reduced to 150 cc/min and the fluorine flow was set at 20 cc/min. These conditions were maintained for approximately 30 hours after which time the nitrogen flow was reduced to 100 cc/min and the reactor was allowed to slowly warm to 45° C. over a 4 hour period. Next, the nitrogen flow was turned off and the reactor was slowly warmed to 70° C. over a 3 hour period. Upon heating to 70° C., the polymer was exposed to pure flourine for an additional hour. Extraction of the sodium fluoride/polymer mixture with approximately 1 liter of 1,1,2-trichlorotrifluoroethane gave 23 g of fluid (45% yield) having the following structure which has been confirmed spectroscopically:

$$[CF_2CF_2OCF_2CF_2OCF_2CF_2OCF_2O]_n$$

Example 4

400 g tetraethylene glycol (2.06 mol), 109 g paraformaldehyde (3.62 mol), 17 g triethylene glycol methyl ether (0.103 mol), 150 ml benzene and 5 g ion exchange resin were allowed to react in a 1 liter flask containing a water separator. After 6 hours, the contents of the flask were filtered and the lights were removed via a vacuum filtration. A 265 g sample of the polymer was mixed with 160 g chloroform and 285 g 1,1,2-trichlorotrifluoroethane. The polymeric solution was metered, over a 22 hour period, into a stirred 10 liter fluorination reactor which contained 1150 g sodium fluoride powder and 4.5 liters of 1,1,2-trichlorotrifluoroethane. The reactor was maintained at 7° C. while 20% fluorine (diluted with nitrogen) was metered into the reactor at a rate sufficient to react with all of the organic entering the reactor. Upon completion of the reaction, the solution was filtered and the liquid fluorination medium was removed via a distillation yielding 422 g (62% yield) of a clear, stable fluid. The product was fractionated into three samples, one which boiled below 200° C. at 0.05 mm Hg (40%), a second which boiled between 200° and 300° C. at 0.05 mm (35%) and a third having a boiling point above 300° C. at 0.05 mm Hg (25%). The intermediate fraction had a viscosity of 33.1 cst. at 20°, 6.3 cst. at 80° and 2.13 cst. at 150° C. The pour point was −79° C. The analysis was consistent with the formula:

$$[CF_2CF_2OCF_2CF_2OCF_2CF_2OCF_2CF_2OCF_2O]_n$$

$^{19}F$ NMR (δ ppm vs $CFCl_3$) −51.8:$CF_2O$; −56.0:$CF_3O$; −88.8, −90.6:$CF_2CF_2O$.

Anal. Calcd. for $C_9F_{18}O_5$: 20.4, C; 64.5, F. Found. 21.0, C; 65.1, F.

Example 5

A mixture of 400 g dipropylene glycol (3.0 mol), 358 g paraformaldehyde (12 mol), 150 ml toluene and 10 g ion exchange resin was refluxed for 5 hours in a stirred 1 liter flask equipped with a water separator. The ion exchange resin was removed prior to distillation of the mixture to 150° C. under a full vacuum to remove any low molecular weight polymer. Approximately 200 g of polymer remained in the flask which was shown by gel permeation chromatography to have an average molecular weight of approximately 3000.

The polymer (280 g) was mixed with 340 ml 1,1,2-trichlorotrifluoroethane and was slowly pumped into a 15 liter stirred reactor over a 24 hour period. The reactor, which contained 5.5 liters of 1,1,2-trichlorotrifluoroethane and 1220 g sodium fluoride powder, was maintained at 10° C. throughout the reaction while 20% fluorine was bubbled through the liquid fluorination medium at a rate just exceeding that required to react with all of the starting material being pumped into the reactor. The reactor contents were filtered and distilled to give 587 g of fluid which was further treated with 50% fluorine at 270° C. to give a fluid which was essentially free of hydrogen. The purified product was fractionated into three samples. The first fraction boiled below 200° C. at 0.05 mm Hg, the second distilled over between 200° and 300° C. at 0.05 mm and the distillation bottoms had a boiling point above 300° C. at 0.05 mm Hg. The second fraction comprised approximately 20% of the total fluid with the majority of the sample having a boiling point below 200° C. at 0.05 mm.

The viscosity of the second fraction at 20° C. was 72.2 cst. (ASTM slope of 0.644). The pour point was −62° C.

$^{19}$F NMR (δ ppm vs CFCl$_3$):−47.3,−49.3,−51.4:CF$_2$O; −54.0, −55.8:CF$_3$O; −79.7:OCF(CF$_3$)CF$_2$O;−81.8,−82.8, −84.7:OCF(CF$_3$)CF$_2$O;−87.3:CF$_3$CF$_2$O;−130.0:CF$_3$CF$_2$O; −140.3,−144.8,−146.0:OCF$_2$CF(CF$_3$)O.

Anal. Calcd. for CF$_3$O[CF$_2$CF(CF$_3$)OCF$_2$CF(CF$_3$)OCF$_2$O]$_n$−CF$_2$CF$_3$: C, 21.02; F, 67.02. Found. C, 21.08; F, 67.08.

Example 6

Using techniques similar to those described in the previous examples, 350 g 1,4 butanediol, 43 g n-propanol and 200 g paraformaldehyde were reacted in benzene to give a fluid which was treated with 85 g acetic anhydride to give 325 g of a polymeric material having a viscosity of 162 cst. at 30° C. Fluorination of 305 g of the fluid in a typical 40° C. fluorination reaction gave 577 g of fluid of which approximately 30% boiled between 200° and 300° C. at 0.05 mm/Hg.

$^{19}$F NMR (δ ppm vs CFCl$_3$):−51.7(f), −82.1(a), −85.4(d), −86.5(c), −125.9(e) and −130.3(b)

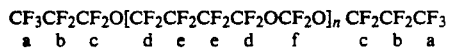

Example 7

Into a 1 liter stirred flask were placed 350 g 1,5 pentanediol (3.4 mol), 23 g n-butanol (0.3 mol), 175 g paraformaldehyde (5.8 mol) and 200 ml benzene. Upon refluxing the mixture for approximately 3 hours with an acid catalyst present, 390 g of a polymeric fluid was obtained which had a viscosity of 450 cst. at 100° F. Fluorination of 310 g of the fluid in a typical fluorination reaction at 14° C. gave 708 g of fluid (80% yield) of which approximately 30% boiled between 200° and 300° C. at 0.05 mm Hg.

$^{19}$F NMR (δ ppm vs CFCl$_3$)−51.3(g), −55.7(c), −81.7 (a), −85.0(d), −122.3(f), −125.5(e) and −126.7(b)

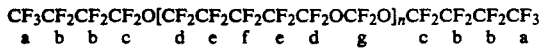

Example 8

Using techniques similar to those described in the previous examples, 350 g 1,6-hexanediol (3.0 mol) 49.3 g n-pentanol (0.56 mol), 134g paraformaldehyde (4.46 mol) were reacted in benzene to give 425 g of a polymeric material having a viscosity of 600 cst. at 100° F. Fluorination of 628 g of the fluid in a typical reaction at 10° C. gave 628 g of fluid (71% yield), of which approximately 30% boiled between 200° and 300° C. at 0.05 mm Hg.

$^{19}$F NMR (δ ppm vs CFCl$_3$):−51.3(i), −56.0(b), −81.7(a), −85.0(f), −85.3(e), −122.7(h), −123.0(c), −125.5(g) and −126.3(d)

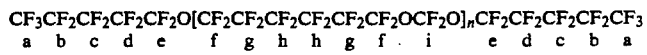

Example 9

Into a 500 ml flask were placed 100 g diethylene glycol (0.94 mol), 55.7 g acetaldehyde diethyl acetal (0.47 mol), 200 ml benzene and 2.5 g acidic ion exchange resin. Attached to the flask was an apparatus designed to continuously extract the by-product ethanol from the refluxing benzene. After approximately 6 hours, the refluxing benzene was essentially free of ethanol and the reaction was assumed to be complete. Filtration of the crude reaction product gave a solution free of the ion exchange resin. Removal of the benzene was accomplished using a rotary evaporator (70° C. bath with a nitrogen purge through the solution).

20 grams of the polymeric product were mixed with 100 ml of methylene chloride and 120 g sodium fluoride powder. On drying the paste, 140 g of a free-flowing powder was obtained. Using the fluorination procedures of Example 3, a 50% yield of the following fluorinated fluid was obtained:

$^{19}$F NMR (δ ppm vs CFCl$_3$): −56.0:CF$_3$O;−86.3:OCF(CF$_3$)O;−87.3:CF$_3$CF$_2$O; −87.7:CF$_3$CF$_2$O;−88.7:OCF$_2$CF$_2$O;−96.3:OCF(CF$_3$)O.

Example 10

Using the procedures detailed in the previous examples, 400 g tetraethylene glycol (2.06 mol) was reacted with 243.5 g acetaldehyde diethyl acetal (2.06 mol) in 250 ml benzene to give 250 g of a polymeric fluid upon refluxing for 6 hours. The polymeric liquid (350 g) was coated on 3555 g of sodium fluoride and placed in a 22 liter rotating drum reactor. After purging for several hours, the reactor was cooled to −10° C. and the fluorine and nitrogen flow rates were set at 350 cc/min and 2 liters/min, respectively. After 25 hours, the nitrogen flow was decreased to 1.5 liter/min. After an additional 14 hours, the nitrogen flow was further reduced to 1 liter/min and the reactor was allowed to slowly warm to 35° C. over a 4 hour period. Upon reaching 35° C., the nitrogen was turned off and the reactor was further warmed to 65° C. prior to terminating the fluorine flow. An oil (371 g) was extracted from the sodium fluoride with 1,1,2-trichlorotrifluoroethane which was determined to have the following structure:

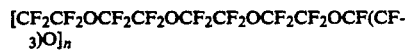

$^{19}$F NMR (δ ppm vs CFCl$_3$) −56.0:CF$_3$O;−86.7:OCF(CF$_3$)O;−87.4:CF$_3$CF$_2$O; −80.0:CF$_3$CF$_2$O;−88.7:OCF$_2$CF$_2$O;−96.7:OCF(CF$_3$)O.

Example 11

A mixture of 600 g 1,5-pentanediol and 30 g potassium hydroxide was heated to 160° C. in a 1 liter flask. Acetylene gas was bubbled through the solution as it was rapidly stirred. The reaction was stopped after 40 hours and the product was washed with water and distilled to give an 85% yield of pentanediol divinyl ether (b.p. 192° C.).

A 1 liter flask cooled to −12° C. was charged with 104 g pentanediol and a trace of methane sulfonic acid. To this solution was added 156 g pentanediol divinyl ether. The solution was stirred rapidly for 2 hours. Then slowly warmed to room temperature over a 6 hour period to give a viscous polymer having viscosity of 650 cst. at 100° F.

The product from the above reaction can be fluorinated in a liquid phase reactor containing 1,1,2-trichlorotrifluoroethane and a sufficient amount of fluorine to complex with all of the hydrogen fluoride formed during the reaction. A perfluoropolyether having the following structure is obtained:

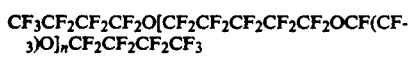

Example 12

Chloroacetaldehyde (50 to 55 wt % in water) was distilled to give a fraction boiling between 87° and 92° C. A 3 liter stirred flask containing 1281 g of the chloroacetaldehyde distillate was placed in a room temperature water bath. While maintaining a temperature below 55° C., 500 ml of concentrated sulfuric acid was slowly added over a one hour period. The mixture was stirred for an additional 3 days at 53° C., then allowed to separate into two phases. The lower phase, containing sulfuric acid, was removed with a separatory funnel while the upper phase was placed into a 3 liter flask equipped with a mechanical stirrer. Concentrated sulfuric acid (200 ml) was carefully added to the solution while the temperature was held below 60° C. with a water bath throughout the addition. The flask was held at 50° C. for an additional 20 hours resulting in a viscous oil being formed. The polymeric product was dissolved in 1 liter methylene chloride and the solution was washed with water several times followed by a rinse with dilute sodium bicarbonate solution. The organic phase was isolated, dried over magnesium sulfate and concentrated to give a dark, viscous product (719 g polychloroacetaldehyde). The product was dissolved in 450 g chloroform and 305 g 1,1,2-trichlorotrifluoroethane to give a solution which was metered over a 22 hour period into a 20° C. fluorination reactor containing 5.5 liters of 1,1,2-trichlorotrifluoroethane. Following the reaction, the solvent was removed leaving behind a fluid with the following structure

| Temperature °F. | Viscosity (cst.) |
|---|---|
| −65 | 1240 |
| 100 | 2.53 |
| 176 | 1.14 |

Example 13

A mixture of 392 g 1,4-cylcohexanedimethanol (2.72 mol), 140 g paraformaldehyde (4.7 mol), 200 ml benzene and 10 g of a H+ ion exchange resin was refluxed for several hours in a flask containing a water separator. A nearly quantitative yield of a sticky solid was obtained after removal of the solvent by distillation.

Fluorination of 263 g of the polymer, diluted with 220 g chloroform and 340 g 1,1,2-trichlorotrifluoroethane in a reactor (10° C.) containing 4.8 liters 1,1,2-trichlorotrifluoroethane and 1300 g sodium fluoride power, gave 440 g of a perfluoropolyether having the following structure:

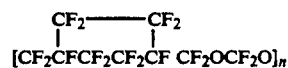

Example 14

Into a 1 liter flask were placed 350 g tetraethylene glycol (1.8 mol), 300 ml benzene, and 10 g ion exchange resin. The mixture was refluxed for 1 hour to remove any moisture present. To the mixture was added 200 ml dimethoxypropane. The distillate was continuously removed over a 2-hour period in 50 ml increments, which were extracted with water to remove the ethanol formed in the reaction. After drying, the distillate was returned to the flask. An additional 200 ml dimethoxypropane was added and the distillate was collected, extracted, dried, and returned to the flask for an additional 3 hours. Removal of the resin and solvent yielded 410 g of a polymeric fluid having a viscosity of 560 cst. at 30° C.

Fluorination of 336 grams of the polyether in a 10° C. reactor containing 5 liters of 1,1,2-trichlorotrifluoroethane and 1420 g sodium fluoride powder gave 642 g of a perfluoropolyether (69.8% yield).

$^{19}$F NMR: (δ ppm vs CFCl$_3$): −55.8(a), −76.3(e), −87.3(d), −88.6(c) and −90.5(b)

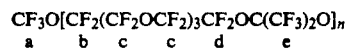

Example 15

A mixture of 300 g pentanediol (2.88 mol), 450 g chloroacetaldehyde/water mixture having a boiling point between 87° and 92° C. and 150 ml benzene was refluxed in a flask containing a water separator. Approximately 5 grams of an acidic ion exchange resin was added to catalyze the reaction. After refluxing for approximately five hours the solution was filtered and the benzene was removed by distillation to leave a residue (approximately 400 g) having a viscosity of 9,700 cst. at 100° F.

Fluorination of 318 g of the polymer, diluted with 235 g chloroform and 375 g 1,1,2-trichlorotrifluoroethane, in a 12° C. reactor containing 5 liters of 1,1,2-trichlorotrifluoroethane and 1200 g sodium fluoride powder gave 623 g (84% yield) of the fluorinated polyether in a 22-hour reaction.

$^{19}$F NMR (δ ppm vs CFCl$_3$) −73.4(h), −74.3(c), −81.6(a), −82.3(d), −87.1(g), −122.1(f), −125.3(e) and −126.3(b)

Equivalents

Those skilled in the art will recognize or be able to ascertain using no more than routine experimentation many equivalents to the specific embodiments of the invention described herein. Such equivalents are intended to be encompassed by the following claims:

We claim:

1. A perhalogenated polyether having an average formula:

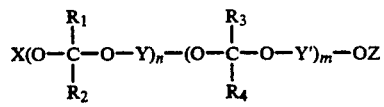

wherein Y and Y' are the same or different and are selected from the group consisting of linear and branched perfluoroalkylenes having at least 2 carbon atoms; perfluoroalkyleneoxyalkylene and perfluoropoly-(alkyleneoxyalkylene) each having alkylene groups containing at least two carbon atoms wherein Y or Y' one or more of the fluorine atoms may be substitute by a halogen atom other than fluorine; wherein X and Z are the same or different and are selected from the group consisting of $-(CF_2)_rCOF$, $-(CF_2)_rOCF_3$, $-(CF_2)_rCOOH$ and $-C_rF_{2r+1-1}Cl_q$, wherein r is an integer from 1 to 12 and q is an integer from 0 to 25; wherein $R_1$, $R_2$, $R_3$ and $R_4$ are the same or different and are selected from the group consisting of $-F$, $-Cl$, $-CF_2Cl$, $-CFCl_2$, $-CCl_3$, perfluoroalkyl of one to ten carbon atoms and perfluoroalkoxyalkyl of one to ten carbon atoms wherein one or more of the fluorine atoms may be substituted by a halogen atom other than fluorine; wherein n is an integer from 2 to 1,000; and wherein m is an integer from 0 to 1,000; provided that when $R_1$, $R_2$, $R_3$ and $R_4$ together are F, then Y and Y' cannot be both $-C_2F_4-$.

2. A perhalogenated polyether of claim 1, wherein Y and Y' are selected from the group consisting of $-C_2F_4-$, $-C_3F_6-$, $-C_4F_8-$, $-C_5F_{10}-$, $-C_6F_{12}-$, $-CF_2CF(CF_3)-$, $-CF_2CF(C_2F_5)-$ and $-CF_2CF(CF_2Cl)-$.

3. A perhalogenated polyether having an average formula:

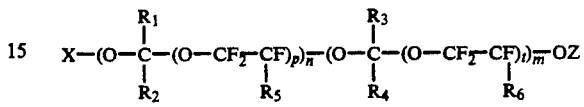

wherein $R_1$, $R_2$, $R_3$, $R_4$, $R_5$ and $R_6$ are the same or different and are selected from the group consisting of $-F$, $-Cl$, $-CF_2Cl$, $-CFCl_2$, $-CCl_3$, perfluoroalkyl of one to ten carbon atoms and perfluoroalkoxyalkyl of one to ten carbon atoms wherein one or more of the fluorine atoms may be substituted by a halogen atom other than fluorine; wherein X and Z are the same or different and are selected from the group consisting of $-(CF_2)_rCOF$, $-(CF_2)_rOCF_3$, $-(CF_2)_rCOOH$ and $-C_rF_{2r+1-q}Cl_q$ wherein r is an integer from 1 to 12 and q is an integer from 0 to 25; wherein n equals 2 to 1000; m is an integer from 1 to 1000; p and t are the same or different and are integers from 1 to 50, provided that when p and t are one and $R_1$, $R_2$, $R_3$ and $R_4$ together are F, then $R_5$ or $R_6$ is a group other than fluorine.

* * * * *